United States Patent [19]

Grayson

[11] Patent Number: 4,579,953

[45] Date of Patent: Apr. 1, 1986

[54] PROCESS FOR THE PRODUCTION OF 6-METHYLNICOTINIC ACID ESTER

[75] Inventor: James I. Grayson, Visp, Switzerland

[73] Assignee: Lonza Ltd., Basle, Switzerland

[21] Appl. No.: 606,228

[22] Filed: May 2, 1984

[30] Foreign Application Priority Data

May 10, 1983 [CH] Switzerland ................. 2542/83

[51] Int. Cl.[4] .......................................... C07D 211/78
[52] U.S. Cl. ................................................ 546/318
[58] Field of Search ................................ 546/320, 318

[56] References Cited

U.S. PATENT DOCUMENTS

| | | | |
|---|---|---|---|
| 2,522,163 | 9/1950 | Cislak et al. | 546/320 |
| 2,749,350 | 6/1956 | Nowlin et al. | 260/295 |
| 2,991,285 | 7/1961 | Feely et al. | 260/283 |
| 2,993,904 | 7/1961 | Mehan et al. | 260/295.5 |

OTHER PUBLICATIONS

Noller, Textbook of Organic Chemistry, W. B. Saunders Co., Philadelphia, 1966, p. 173.

Castle, et al., J. Org. Chem., vol. 24 (1959), p. 1190.
Murahashi, et al., Chem. Abst., vol. 45, 1951, 9054g.

Primary Examiner—Henry R. Jiles
Assistant Examiner—Robert C. Whittenbaugh
Attorney, Agent, or Firm—Fisher, Christen & Sabol

[57] ABSTRACT

A process for the production of 6-methylnicotinic acid ester by oxidation of 2-methyl-5-ethylpyridine at an elevated temperature. Specifically, 2-methyl-5-ethylpyridine is mixed while cooling with at least a molar quantity of sulfuric acid. The mixture is heated to a temperature of 140° to 225° C. At least 3 moles of nitric acid per mole of educt is added to the heated mixture in such a way that water and/or diluted nitric acid are continuously distilled off. The distillation after addition of the nitric acid which is needed for the oxidation is continued until all of the water and all of the nitric acid are removed. Subsequently the reaction mixture is mixed with an alcohol and the alcoholic reaction mixture is heated until the acids contained in the reaction mixture are esterified. The 6-methylnicotinic acid ester is isolated from the ester mixture.

14 Claims, No Drawings

PROCESS FOR THE PRODUCTION OF 6-METHYLNICOTINIC ACID ESTER

BACKGROUND OF THE INVENTION

1. Field of the Invention

The invention relates to a process for the production of 6-methylnicotinic acid by oxidation of 2-methyl-5-ethylpyridine at an elevated temperature.

2. Prior Art 6-methylnicotinic acid ester has been produced by the oxidation of 2-methyl-5-ethylpyridine. Either potassium permanganate or nitric acid is used as an oxidation agent. The potassium permanganate process [J. Org. Chem. 24 (1959), 1190] has the disadvantage that large quantities of water and potassium permanganate and long reaction times are needed. Thus. 10.9 kg of potassium permanganate and 364 liters of water were needed per kg of end product. The reaction time was about 5 days and the yield was around 69 percent. According to C. A., Vol. 45 (1951), 9055, 2-methyl-5-ethylpyridine was converted with nitric acid in the presence of ammonium vanadate into 6-methylnicotinic acid, the latter being isolated as the copper salt. The reaction time was 3 days, and the yield was 51 percent. In U.S. Pat. No. 2,991,285, the preceding method was modified and the 6-methylnicotinic acid was isolated using ion exchange. In this case, the yield amounted to 46 percent. $SeO_2$ with introduction of air has also already been described as the catalyst for the nitric acid oxidation (see U.S. Pat. No. 2,749,350). The product was isolated as the copper salt in a yield of 68 percent. After decomposition of the copper salt, the yield of 6-methylnicotinic acid was about 47 percent. The nitric acid oxidation has also already been carried out under pressure and at a temperature of from 130° to 180° C. (see U.S. Pat. No. 2,993,904). In that case, only extremely low yields of 6-methyl nicotinic acid were achieved.

BROAD DESCRIPTION OF THE INVENTION

It is an object of the invention to eliminate the disadvantages of the known processes described above and to provide a technically feasible process. Other objects and advantages are set out herein or are obvious herefrom to one ordinarily skilled in the art.

The objects and advantages of the invention are achieved by the process of the invention.

The invention involves a process for the production of 6-methylnicotinic acid ester by oxidation of 2-methyl-5-ethylpyridine at an elevated temperature. The process includes mixing 2-methyl-5-ethylpyridine while cooling with at least a molar quantity of sulfuric acid. The mixture is heated to a temperature of 140° to 225° C. At least 3 moles of nitric acid per mole of educt is added to the heated mixture, in such a way that water and/or diluted nitric acid are continuously distilled off. The distillation after addition of the nitric acid which is needed for the oxidation is continued until all of the water and all of the nitric acid are removed. Subsequently the reaction mixture is mixed with an alcohol and the alcoholic reaction mixture is heated until the acids contained in the reaction mixture are esterified. The 6-methylnicotinic acid ester is isolated from the ester mixture.

DETAILED DESCRIPTION OF THE INVENTION

In the invention process, one mole of the 2-methyl-5-ethylpyridine is first mixed with 1 to 5 mole, preferably 2 to 4 mole, of 20 to 100 percent sulfuric acid at a temperature of from 0° to 100° C. The mixture is heated to 140° to 225° C., preferably to 150° to 170° C. When using sulfuric acid having a concentration of less than 100 percent, the corresponding quantity of water is distilled off. Nitric acid, having a concentration of 20 to 70 percent, in a quantity of 3 to 10 mole, preferably 6 to 9 moles, per mole of 2-methyl-5-ethylpyridine is continuously; such that the water and/or the diluted nitric acid formed is continuously distilled off. This takes 2 to 11 hours, normally 5 to 7 hours. When the addition of the nitric acid is completed, the reaction mixture is still kept at the reaction temperature or higher, for example, up to 190° C., until all of the water and all of the nitric acid is distilled off. Normally this takes 15 to 30 minutes. The diluted nitric acid which has been distilled off during the reaction can be reconcentrated and returned to the process.

The oxidation may be carried out with or without addition of oxidation catalysts, such as ammonium vanadate, tin chloride, cobalt acetate. When an oxidation catalyst is used, the amount of oxidation catalyst used is less than 5 g, preferably less than 2 g, per mole of 2-methyl-5-ethylpyridine.

After distilling off the nitric acid and the water, the mixture remaining behind in the reaction vessel, which contains mainly 2-methyl-5-ethylpyridine, 6-methylnicotinic acid and isocinchomeronic acid, all of them as sulfuric acid salts, is mixed with an alcohol. The alcoholic mixture is heated to a temperature of from 25° C. up to the reflux point of the alcohol. The temperature is maintained until the acids are esterified.

The alcohol is selected depending on the ester desired. Primary, secondary or tertiary alcohols and aliphatic or non-aliphatic alcohols can be used. For example, the alcohol can be a lower alkanol such as methanol, ethanol, isopropanol, n-butanol or t-butanol. The quantity of alcohol used is at least 1 mole, preferably 5 to 10 moles, per mole of 2-methyl-5-ethylpyridine.

The solution present after the esterification is concentrated, neutralized and extracted. Any suitable concentration scheme can be used. Any suitable base can be used for the neutralization. Examples of the organic solvent which can be used effectively for the extraction are methylene chloride, chloroform, ether and toluene. After fractional distillation of the extract, the individual products methylethylpyridine, 6-methylnicotinic acid ester and isocinchomeronic acid diester are obtained in yields of about 10 to 12 percent, 65 to 70 percent and 3 to 5 percent, respectively.

By way of summary, the process of the invention involves producing 6-methylnicotinic acid ester by the oxidation of 2-methyl-5-ethylpyridine.

EXAMPLE 1

225.0 g (2.26 mole) of 96 percent sulfuric acid and 0.5 g (4.3 mmole) of ammonium vanadate were put into a 1.5 liter sulfurizing flask. The flask was cooled and 92.7 g (0.75 mole) of 98 percent 2-methyl-5-ethylpyridine was added dropwise within a 25 minute period. The stirred reaction mixture was heated to 160° C. and, during a 5 hour 30 minute period, 600.0 g (6.2 mole) of 65 percent nitric acid was added dropwise so that the reaction temperature remained between 155° and 160° C. During this time, 445.0 g of nitric acid was continuously distilled off. The distillate contained 46.9 percent nitric acid which corresponds to a consumption during the reaction of 2.89 mole of nitric acid. After completion of the addition of the nitric acid, the reaction mixture was heated for 15 minutes to 190° C. in order to distill off unreacted nitric acid. Subsequently, the reaction mixture was cooled to below 100° C. and was poured into 300 ml of ethanol. The reaction flask was washed with 100 ml of ethanol. The entire ethanol solution was heated for 6 hours under reflux. The ethanol was distilled off, and the residue was poured onto 300 g of ice and neutralized with 25 percent ammonia solution. The product was extracted 3 times with 100 ml of methylene chloride. The methylene chloride extracts were evaporated and the residue was analyzed by means of gas chromatography. The GC-analysis showed a yield of 2-methyl-5-ethylpyridine of 11.8 percent, of 6-methylnicotinic acid ethyl ester of 67.9 percent and of isocinchomeronic acid diethyl ester of 3.5 percent. All the gas chromatographic analyses were carried out with the use of an internal standard and with due consideration of surface correction factors.

The crude products from five such experiments were distilled, whereby 57.1 g of 2-methyl-5-ethylpyridine (12.6 percent yield) was distilled off first, followed by 409.9 g of 98.3 percent 6-methylnicotinic acid ethyl ester having a boiling point of 121° to 125° C. at 20 mm Hg (65.0 percent yield). The selectivity of the reaction giving 6-methylnicotinic acid ethyl ester was 74.4 percent.

EXAMPLE 2

This example was conducted in the same manner as Example 1 except that methanol was used instead of ethanol. The crude products from five such experiments were distilled, whereby 53.5 g of 2-methyl-5-ethylpyridine (11.7 percent yield) was distilled off first, followed by 404.7 g of 97.6 percent 6-methylnicotinic acid methyl ester having a boiling point of 112° to 115° C. at 20 mm Hg (69.7 percent yield). The selectivity of the reaction giving 6-methylnicotinic acid methyl ester was 78.9 percent.

EXAMPLE 3

This example was conducted in the same manner as Example 1. 630.0 g of 65 percent nitric acid was added and the reaction temperature was 160° to 165° C. The product was esterified with 400 ml of isopropanol for 18 hours at reflux temperature. The crude ester was distilled, whereby 5.0 g of 2-methyl-5-ethylpyridine (5.6 percent yield) was distilled off first, followed by 77.5 g of 97.2 percent 6-methylnicotinic acid isopropyl ester having a boiling point of from 70° to 72° C. at 0.6 mm Hg (56.1 percent yield). The selectivity of the reaction giving 6-methylnicotinic acid isopropyl ester was 59.4 percent.

EXAMPLE 4

This example was conducted in the same manner as Example 1. 630.0 g of 65 percent nitric acid were added and the reaction temperature was 160° to 165° C. The product was esterified with 400 ml of n-butanol for 18 hours at reflux temperature. The crude ester was distilled, whereby 5.7 g of 2-methyl-5-ethylpyridine (6.3 percent yield) was distilled off first, followed by 92.3 g of 97.3 percent 6-methylnicotinic acid n-butyl ester having a boiling point of 95° to 97° C. at 0.6 mm Hg (63.2 percent yield). The selectivity of the reaction giving 6-methylnicotinic acid n-butyl ester was 67.4 percent.

EXAMPLES 5 to 15

Examples 5 to 15 were conducted in basically the same manner as in Example 1. The reaction conditions and the yields (according to gas chromatographic analysis of the raw products) are summarized in the following Table:

TABLE

| Example No. | Educts | | | | Reaction temperature (°C.) | Nitric acid dosage time (hrs.) | Esterification time (hrs.) | Yield | | | Selectivity of 6-methylnicotinic acid ethyl ester, (%) |
|---|---|---|---|---|---|---|---|---|---|---|---|
| | 2-methyl-5-ethyl pyridine (g) | Sulfuric acid (g) | Ammonium vanadate (g) | Nitric acid (g) | | | | 2-methyl-5-ethyl pyridine (%) | 6-methyl-nicotinic acid ethyl ester (%) | Isocincho-meronic acid diethyl ester (%) | |
| 5 | 92.7 | 200 | 1.0 | 582 | 150°–155° | 6 | 18 | 8.1 | 69.9 | 4.3 | 76.1 |
| 6 | 92.7 | 200 | 0.5 | 679 | 180°–185° | 5 | 18 | 0.1 | 62.0 | 14.3 | 62.1 |
| 7 | 92.7 | 250 | 1.8 | 582 | 145°–150° | 5½ | 18 | 6.4 | 69.4 | 5.1 | 72.6 |
| 8 | 92.7 | 225 | 3.6 | 630 | 150°–155° | 5½ | 18 | 0.3 | 63.5 | 10.4 | 63.7 |
| 9 | 92.7 | 225 | — | 679 | 165°–170° | 6 | 18 | 25.0 | 57.7 | 2.8 | 76.9 |
| 10 | 92.7 | 250 | — | 630 | 190°–195° | 5½ | 60 | 7.9 | 61.7 | 9.8 | 67.0 |
| 11 | 92.7 | 300 | 0.3 | 582 | 165°–170° | 5 | 18 | 14.2 | 63.9 | 2.6 | 74.5 |
| 12 | 92.7 | 225 | — | 291 | 175°–180° | 2 | 18 | 48.9 | 35.8 | 3.9 | 70.0 |
| 13 | 92.7 | 225 | — | 654 | 175°–180° | 11 | 18 | 1.0 | 67.6 | 12.4 | 68.3 |
| 14 | 92.7 | 112 | — | 291 | 220°–225° | 2 | 18 | 28.5 | 27.5 | 6.9 | 38.5 |
| 15 | 92.7 | 225 | — | 654 | 220°–225° | 4¼ | 18 | 10.9 | 37.3 | 19.7 | 41.9 |

EXAMPLE 16

150.0 g (1.5 mole) of 96 percent sulfuric acid and 0.9 g (7.5 mmole) of ammonium vanadate were put into a 1.5 liter sulfurizing flask. The flask was cooled and 92.7 g (0.75 mole) of 98 percent 2-methyl-5-ethylpyridine was added dropwise within 20 minutes. The stirred reaction mixture was heated to 200° C. and 509 g (5.25 mole) of 65 percent nitric acid was added dropwise over 5 hours so that the reaction temperature remained between 200° and 205° C. During this time, nitric acid was continuously distilled off. After the end of the addition of the nitric acid, the reaction was heated for 15 minutes at 200° C. and subsequently cooled to 120° C. 150 ml of water was added and then the reaction mixture was poured into 150 ml of water. The reaction mixture was washed twice with 100 ml of water and the collected water-fractions were cooled to 0° C. 41.8 g of isocinchomeric acid was filtered off (33.3 percent yield). The mother liquors were evaporated and the residue was dissolved in 500 ml of methanol. The solution was heated under reflux for 18 hours, and subsequently worked up as in Example 1. The gas chromatographic analysis of the raw ester mixture showed a yield of 2-methyl-5-ethylpyridine of 0.4 percent, of 6-methylnicotinic acid ethyl ester of 50.1 percent and of isocinchomieric acid diethyl ester of 3.2 percent. The selectivity of the reaction giving 6-methylnicotinic acid ethyl ester was 50.3 percent.

What is claimed is:

1. A process for the production of 6-methylnicotinic acid ester by the oxidation of 2-methyl-5-ethylpyridine at an elevated temperature, characterized in that 2-methyl-5-ethylpyridine is mixed while cooling with at least a molar quantity of sulfuric acid, the mixture is heated to a temperature of 140° to 225° C., at least 3 moles of nitric acid per mole of educt is added to the heated mixture in such a way that water and/or diluted nitric acid is continuously distilled off, the distillation after addition of the nitric acid which is needed for the oxidation is continued until all of the water and all of the nitric acid are removed, the reaction mixture is mixed with an alcohol, the alcoholic reaction mixture is heated until the acids contained in the reaction mixture are esterified, and the 6-methylnicotinic acid ester is isolated from the ester mixture.

2. The process as claimed in claim 1 wherein 1 to 5 moles of sulfuric acid, having a concentration of from 20 to 100 percent, is used per mole of 2-methyl-5-ethylpyridine.

3. The process as claimed in claim 1 wherein 2 to 4 moles of sulfuric acid, having a concentration of from 20 to 100 percent, is used per mole of 2-methyl-5-ethylpyridine.

4. The process as claimed in claim 1 wherein the mixture containing the sulfuric acid is heated to a temperature of 150° C. to 170° C. before the nitric acid is added.

5. The process as claimed in claim 1 wherein 3 to 10 moles of nitric acid, having a concentration of 20 to 100 percent, is used per mole of 2-methyl-5-ethylpyridine.

6. The process as claimed in claim 1 wherein 6 to 9 moles of nitric acid, having a concentration of 20 to 100 percent, is used per mole of 2-methyl-5-ethylpyridine.

7. The process as claimed in claim 1 wherein the oxidation is carried out in the presence of an oxidation catalyst.

8. The process as claimed in claim 7 wherein the oxidation is ammonium vanadate, tin chloride or cobalt acetate.

9. The process as claimed in claim 7 wherein less than 5 grams of the oxidation catalyst is used per mole of 2-methyl-5-ethylpyridine.

10. The process as claimed in claim 7 wherein less than 2 grams of the oxidation catalyst is used per mole of 2-methyl-5-ethylpyridine.

11. The process as claimed in claim 1 wherein the alcohol is methanol, ethanol, isopropanol, n-butanol or t-butanol.

12. The process as claimed in claim 1 wherein 5 to 10 moles of the alcohol is used per mole of 2-methyl-5-ethylpyridine.

13. The process as claimed in claim 1 wherein the 6-methyl nicotinic acid ester is isolated by concentrating the ester mixture, neutralizing the sulfuric acid with a base, extracting the esters with an organic solvent and fractionating the extract.

14. The process as claimed in claim 13 wherein the organic solvent is methylene chloride, chloroform, ether or toluene.

* * * * *